(12) United States Patent
Method

(10) Patent No.: US 11,011,262 B2
(45) Date of Patent: May 18, 2021

(54) RETROFITTED CONTINUOUS PASSIVE MOTION DEVICES

(71) Applicant: Kinex Medical Company, LLC, Waukesha, WI (US)

(72) Inventor: Victor Gregory Method, Park City, UT (US)

(73) Assignee: Kinex Medical Company, LLC, Waukesha, WI (US)

( * ) Notice: Subject to any disclaimer, the term of this patent is extended or adjusted under 35 U.S.C. 154(b) by 1059 days.

(21) Appl. No.: 15/286,346

(22) Filed: Oct. 5, 2016

(65) Prior Publication Data
US 2017/0100296 A1    Apr. 13, 2017

Related U.S. Application Data

(60) Provisional application No. 62/238,578, filed on Oct. 7, 2015.

(51) Int. Cl.
*G16H 20/30* (2018.01)
*A61H 1/02* (2006.01)
(Continued)

(52) U.S. Cl.
CPC ........... *G16H 20/30* (2018.01); *A61B 5/1121* (2013.01); *A61B 5/486* (2013.01); *A61B 5/4833* (2013.01);
(Continued)

(58) Field of Classification Search
CPC .......... A61H 1/00; A61H 1/02; A61H 1/0218; A61H 1/0237; A61H 1/0259; A61H 1/024; A61H 2201/0107; A61H 2201/5005; A61H 2201/5015; A61B 5/1121; A61B 5/1124; A61B 5/4833; A61B 5/486; A61B 5/6812; A61B 5/743; A61B 2205/09;
(Continued)

(56) References Cited

U.S. PATENT DOCUMENTS 2,763,261 A    9/1956 Louis
2,924,214 A    2/1960 Zak
(Continued)

FOREIGN PATENT DOCUMENTS

JP    H09224990    9/1997

OTHER PUBLICATIONS

Search Report dated May 9, 2019 from EP Application No. 16854397.3.
(Continued)

*Primary Examiner* — Timothy A Stanis
*Assistant Examiner* — Matthew R Moon
(74) *Attorney, Agent, or Firm* — Brian G. Gilpin; Godfrey & Kahn, S.C.

(57) ABSTRACT

A method for gathering information relating to the use of a continuous passive motion device can include receiving usage information from a continuous passive motion device processing unit. The usage information can include at least one duration of time that the continuous passive motion device was used. The method can also include storing the usage information such that the usage information is available within a historical dataset. Additionally, the method can include displaying at least a portion of the usage information from the historical dataset on a graphical user interface.

1 Claim, 16 Drawing Sheets

(51) Int. Cl.
*A61B 5/00* (2006.01)
*A61B 5/11* (2006.01)
*G16H 40/67* (2018.01)
*A63B 23/035* (2006.01)
*A63B 24/00* (2006.01)
*H04W 4/80* (2018.01)

(52) U.S. Cl.
CPC ............ *A61B 5/6812* (2013.01); *A61B 5/743* (2013.01); *A61H 1/02* (2013.01); *A61H 1/024* (2013.01); *A61H 1/0218* (2013.01); *A61H 1/0237* (2013.01); *A61H 1/0259* (2013.01); *A63B 23/03508* (2013.01); *A63B 24/0087* (2013.01); *G16H 40/67* (2018.01); *A61B 5/1124* (2013.01); *A61B 2505/09* (2013.01); *A61H 2201/0107* (2013.01); *A61H 2201/5005* (2013.01); *A61H 2201/5015* (2013.01); *H04W 4/80* (2018.02)

(58) Field of Classification Search
CPC .......... A63B 23/03508; A63B 24/0087; G16H 20/30; G16H 40/67; H04W 4/80
See application file for complete search history.

(56) References Cited

U.S. PATENT DOCUMENTS

| | | | |
|---|---|---|---|
| 4,089,330 A | 5/1978 | Nicolosi | |
| 4,229,001 A | 10/1980 | Roman | |
| 4,365,623 A * | 12/1982 | Wilhelm | A61H 1/0218 602/32 |
| 4,489,713 A | 12/1984 | Latenser | |
| 4,538,595 A | 9/1985 | Hajianpour | |
| 4,549,534 A | 10/1985 | Zagorski | |
| 4,558,692 A * | 12/1985 | Greiner | A61H 1/0255 601/33 |
| 4,621,620 A | 11/1986 | Anderson | |
| 4,665,899 A | 5/1987 | Farris | |
| 4,671,257 A | 6/1987 | Kaiser | |
| 4,751,917 A | 6/1988 | Ruf | |
| 4,825,852 A | 5/1989 | Genovese | |
| 4,834,073 A | 5/1989 | Bledsoe | |
| 4,844,454 A | 7/1989 | Rogers | |
| 4,848,325 A | 7/1989 | Lillie | |
| 4,946,053 A | 7/1990 | Smith | |
| 4,982,832 A | 1/1991 | Morris | |
| 5,035,233 A | 7/1991 | Ruf | |
| 5,050,589 A | 9/1991 | Engle | |
| 5,280,783 A | 1/1994 | Focht | |
| 5,303,716 A | 4/1994 | Mason et al. | |
| 5,312,315 A | 5/1994 | Mortensen et al. | |
| 5,352,185 A | 10/1994 | Blauth | |
| 5,399,147 A | 3/1995 | Kaiser | |
| 5,509,894 A | 4/1996 | Mason et al. | |
| 5,582,579 A | 12/1996 | Chism et al. | |
| 5,687,742 A | 11/1997 | Johnson | |
| 5,901,581 A | 5/1999 | Chen | |
| 6,217,532 B1 | 4/2001 | Blanchard | |
| 6,221,032 B1 | 4/2001 | Blanchard et al. | |
| 6,221,033 B1 | 4/2001 | Blanchard | |
| 6,224,521 B1 | 5/2001 | Foucault | |
| 6,267,735 B1 * | 7/2001 | Blanchard | A61H 1/024 601/23 |
| 6,450,930 B1 | 9/2002 | Kroke | |
| 6,962,570 B2 | 11/2005 | Callanan | |
| 7,857,779 B2 | 12/2010 | Gondringer | |
| 7,874,968 B2 | 1/2011 | Foucault | |
| 8,128,532 B2 * | 3/2012 | Chen | G06Q 10/02 482/8 |
| 9,398,994 B2 * | 7/2016 | McBean | A61F 5/0127 |
| 9,669,249 B2 * | 6/2017 | Marti | A63B 71/0622 |
| 10,179,078 B2 * | 1/2019 | Bhugra | A61H 1/024 |
| 2002/0045844 A1 | 4/2002 | Berry | |
| 2004/0053746 A1 * | 3/2004 | Chen | A63B 22/0242 482/1 |
| 2004/0127821 A1 | 7/2004 | Ou et al. | |
| 2006/0064044 A1 | 3/2006 | Schmehi | |
| 2007/0249972 A1 | 10/2007 | Ripperger | |
| 2009/0227911 A1 | 9/2009 | Srivastava | |
| 2009/0275868 A1 * | 11/2009 | Steingart | A61H 1/024 601/34 |
| 2010/0313897 A1 | 12/2010 | Schaeffer | |
| 2013/0162907 A1 | 6/2013 | Kim | |
| 2014/0094721 A1 * | 4/2014 | Diallo | A61H 1/024 601/5 |
| 2015/0148714 A1 * | 5/2015 | Bonutti | A61F 5/0102 601/5 |

OTHER PUBLICATIONS

Non-Final Office Action in U.S. Appl. No. 13/572,690 dated Mar. 26, 2015.
International Search Report and Written Opinion for PCT/US2013/054480, dated Nov. 20, 2013.
Non-Final Office Action in U.S. Appl. No. 13/053,973 dated Feb. 14, 2013.
Notice of Allowance in U.S. Appl. No. 13/572,690 dated Sep. 22, 2016.
Final Office Action in U.S. Appl. No. 13/572,690 dated Jan. 5, 2016.

* cited by examiner

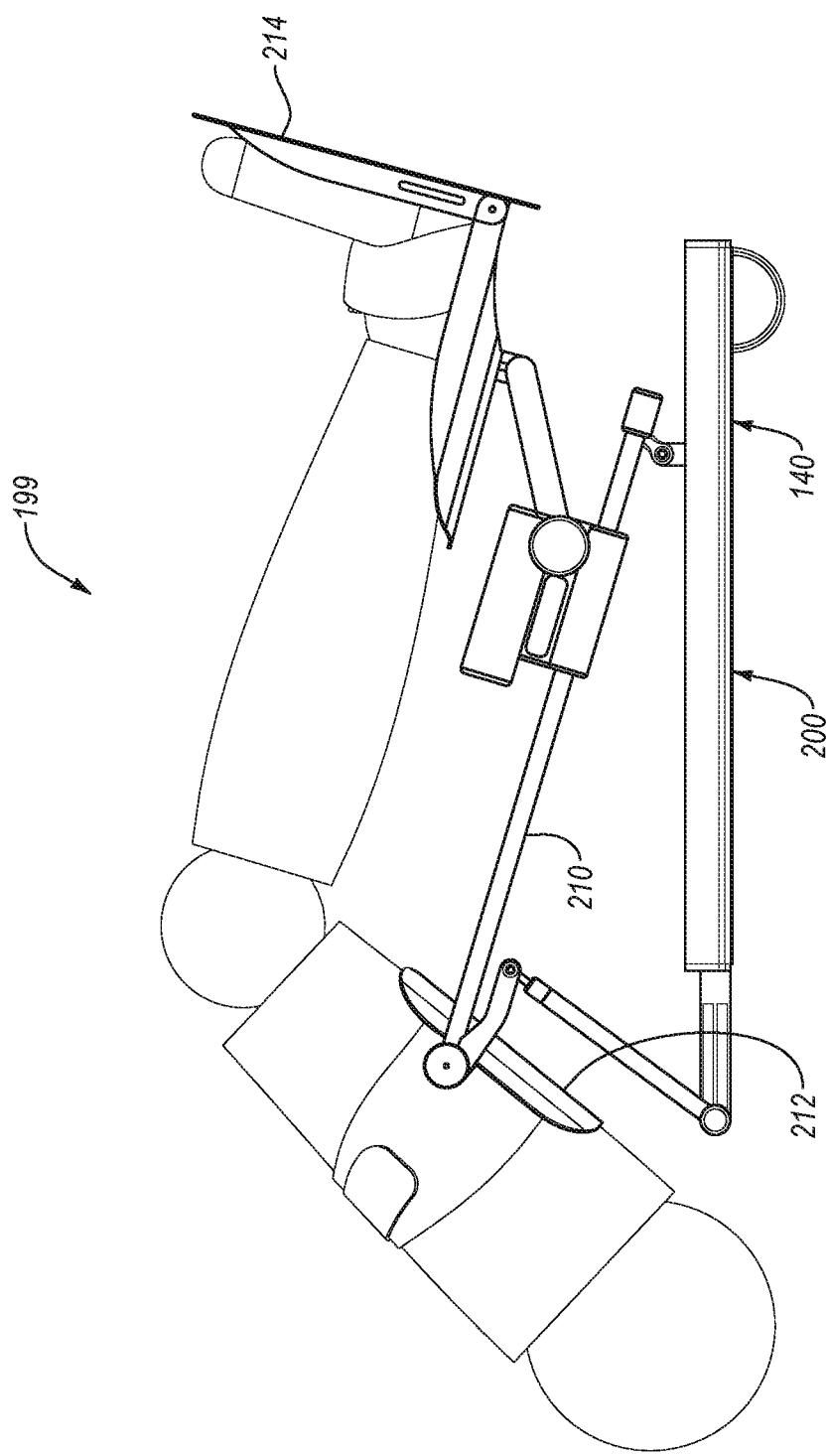

RETROFITTED CONTINUOUS PASSIVE MOTION DEVICES

CROSS-REFERENCE TO RELATED APPLICATIONS

This application claims priority to and the benefit of U.S. Provisional Patent Application Ser. No. 62/238,578, filed Oct. 7, 2015, and entitled "RETROFITTED CONTINUOUS PASSIVE MOTION DEVICES," the disclosure of which is incorporated herein by this reference in its entirety.

BACKGROUND

The present disclosure relates to devices and supports for stretching a human limb. More particularly, the present disclosure pertains to devices used for supporting a leg while applying flexion or extension forces of the type used for rehabilitating or exercising a knee joint.

Devices for stretching joints are commonly used by physical therapists for knee rehabilitation following injury or operation. A patient typically must undergo a physical therapy rehabilitation program for several weeks or months following such an event. During rehabilitation, the patient generally performs stretching exercises multiple times a day to develop strength and flexibility for the affected joint. Typically, a patient may undergo at least two types of knee rehabilitation exercises.

Flexion of the leg occurs by bending the knee joint to decrease the angle between the upper and lower portions of the leg. Flexion force is typically applied to a patient's leg by a physical therapist. During a flexion exercise, the patient lies face-up on a therapy table or other surface while a therapist applies force to the lower leg, bending it about the knee joint toward the upper leg. A structure may be placed under the knee to support the leg during flexion. Once the lower leg and upper leg are oriented at an optimal stretching angle, usually less than ninety degrees, the therapist then attempts to maintain the applied force and hold the leg at a static angle for a period of time, ranging from a few seconds to a few minutes. After the desired time has elapsed, the physical therapist then releases the applied flexion force in a controlled manner, and the leg is extended to a more relaxed position. This type of flexion exercise may be repeated several times during a single therapy session.

Similarly, extension exercises are typically also required for rehabilitation following a knee injury or operation. Extension of the leg occurs by straightening the leg at the knee joint, causing the angle between the upper and lower leg to increase. During an extension exercise, a physical therapist typically holds the lower portion of the leg or the foot of the patient in an elevated position while the patient lies face-up on a therapy table. The therapist then pushes the knee or upper part of the leg downward toward the table, causing the leg to straighten. When the leg is straightened to an optimal stretching angle, the therapist then attempts to statically maintain that position for a period of time. After the stretch is complete, the therapist then slowly releases the extension force applied to the leg, allowing the leg to return to a natural, relaxed position. This stretching exercise may also be repeated several times during a therapy session.

Devices for application of flexion or extension pressure to a patient's leg are known in the art. Such devices are commonly capable of providing either flexion or extension pressure, but not both. Such devices are also typically mounted to a table, and are not portable for use in a user's home. Also, rehabilitation therapy often requires a patient to visit a therapist's office several times a week. These trips can interfere with a patient's personal or work schedule and can create additional expense. A portable, easy-to-use stretching device would reduce the need for frequent visits to a therapist's office by allowing a user to perform flexion and extension exercises at home. A single portable device capable of providing both flexion and extension pressure without requiring extensive adjustment between modes is desired.

The application of flexion or extension force to the patient's leg can cause severe pain to the patient. During stretching, the therapist must communicate with the patient to avoid applying excessive force. The force feedback loop between the patient and the therapist necessarily causes fluctuation in the magnitude of applied pressure. Even minor fluctuations in the applied pressure, can detract from the rehabilitative effect of the exercise. Rapid or unsteady changes in applied force can cause injury to the patient. For optimal effectiveness, steady force application and steady force release are preferred. A device that allows the patient to control the applied force during both stretching and release is desired.

It may also be desirable to be able to track a patient's use of a device. For example, a doctor may prescribe that a patient use the particular device for a specific number of hours a day. Both the doctor and a participating insurance company may desire to review the data to ensure that the device is being used and is effective for rehabilitation.

Accordingly, there remains room for improvement with rehabilitation devices.

BRIEF SUMMARY OF THE INVENTION

Implementations of the present invention comprise systems, methods, and apparatus configured to gather usage information from a continuous passive motion device. In particular, implementations of the present invention comprise systems and apparatus for retrofitting a conventional continuous passive motion device, such that the retrofitted continuous passive motion device is able to communicate usage information to a general purpose-computing device. Additionally, implementations of the present invention provide a software application and user interface for controlling and viewing information from a continuous passive motion device.

Implementations of the present invention include a method for gathering information relating to the use of a continuous passive motion device. The method can comprise receiving usage information from a continuous passive motion device processing unit. The usage information can comprise at least one duration of time that the continuous passive motion device was used. The method can also comprise storing the usage information such that the usage information is available within a historical dataset. Additionally, the method can comprise displaying at least a portion of the usage information from the historical dataset on a graphical user interface.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3A-3B depict various implementations of the continuous passive motion device of FIG. 2;

DETAILED DESCRIPTION OF THE PREFERRED EMBODIMENTS

The present invention extends to systems, methods, and apparatus configured to gather usage information from a continuous passive motion device. In particular, implementations of the present invention comprise systems and apparatus for retrofitting a conventional continuous passive motion device, such that the retrofitted continuous passive motion device is able to communicate usage information to a general purpose-computing device. Additionally, implementations of the present invention provide a software application and user interface for controlling and viewing information from a continuous passive motion device.

Accordingly, implementations of the present invention provide a simple and efficient way for patients, health care providers, and insurance companies to access usage information relating to a continuous passive motion device. For example, an insurance company may require proof that a continuous passive motion device was used and/or is effective before issuing payment for the device. In at least one implementation of the present invention, the usage information can easily be provided to the insurance company for verification. Conventional continuous passive motion devices, in contrast, provide no method of usage data gathering, and therefore, are unable to provide the requested information to insurance companies.

Figure 1:
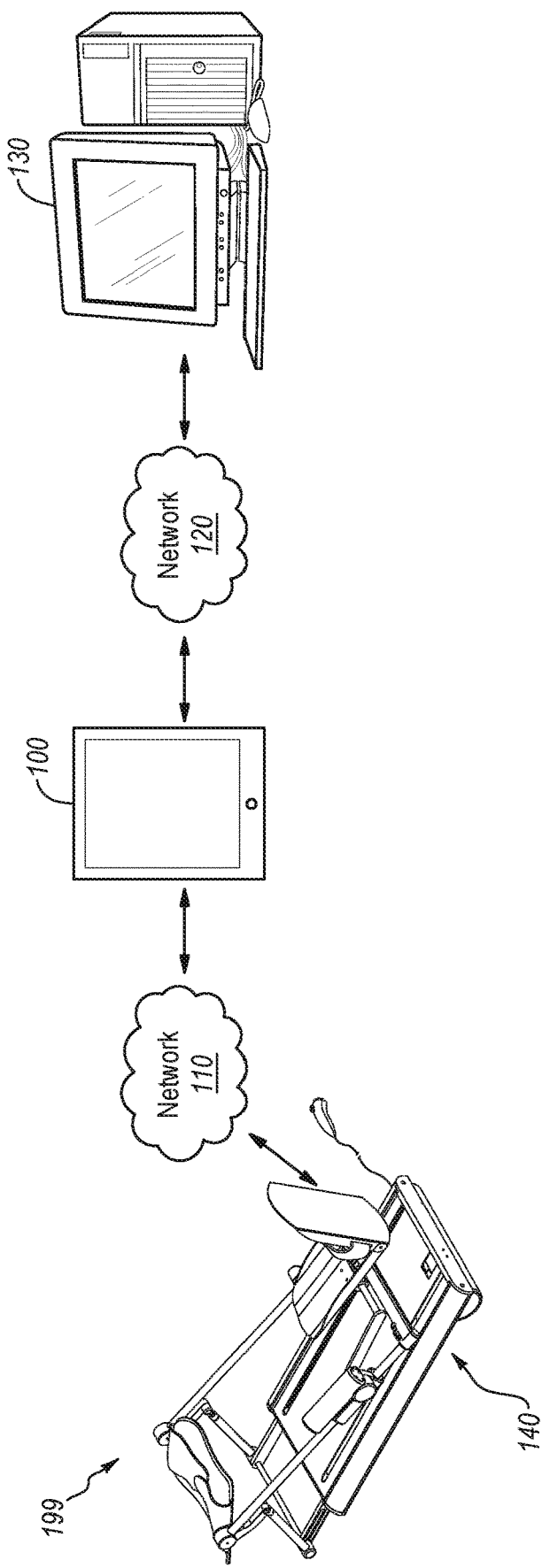
FIG. 1 provides a schematic view of system in accordance with an embodiment of the present invention.

Referring now to the Figures, FIG. 1 depicts a continuous passive motion device 199 in communication with a mobile computing device 100 through a network 110. In particular, the continuous passive motion device 199 comprises a processing unit 140 that is integrated within the device. The processing unit 140 can comprise one or more circuit boards, including circuitry for wireless communications. For example, the processing unit 140 can comprise a BLUETOOTH component that is configured to communicate with a mobile computing device 100 that comprises a tablet.

In at least one implementation, the mobile computing device 100 can comprise a variety of different devices including, but not limited to, a laptop computer, a smart phone, a personal digital assistant, or other similar device. Additionally, in at least one implementation, the continuous passive motion device 199 can be in communication with any general purpose-computing device, such as a desktop computer, a server, a mobile computing device 100, or some other computing device.

As depicted in FIG. 1, in at least one implementation, the mobile computing device 100 can communicate with a server 130 through a network 120. Network 120 can comprise the Internet, a local area network, a WAN, or any other network structure. The mobile computing device 100 can communicate various usage information from the continuous passive motion device 199 to the server 130.

Figure 2:
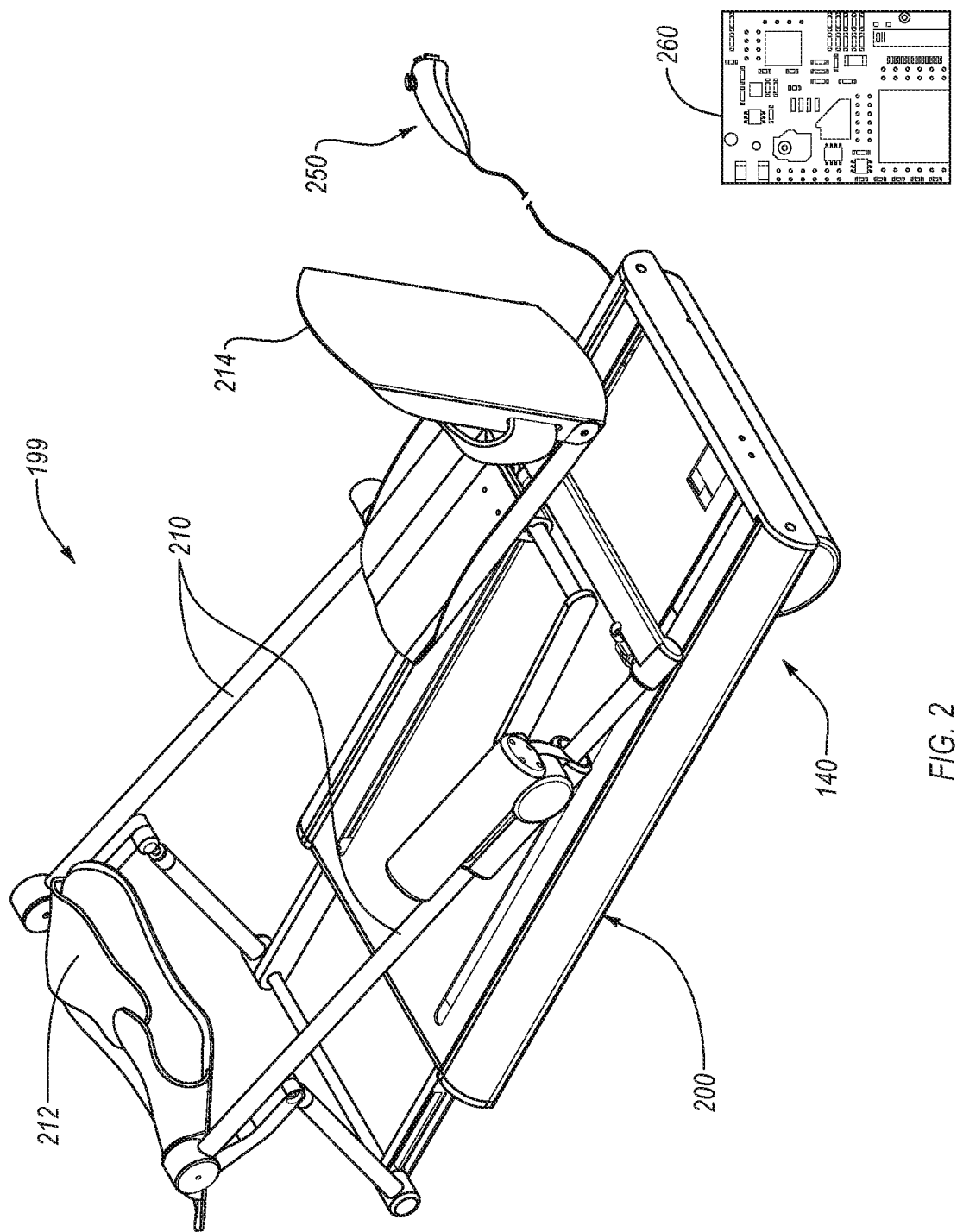
FIG. 2 provides a perspective view of a continuous passive motion device in accordance with an embodiment of the present invention.
Figure 3B:
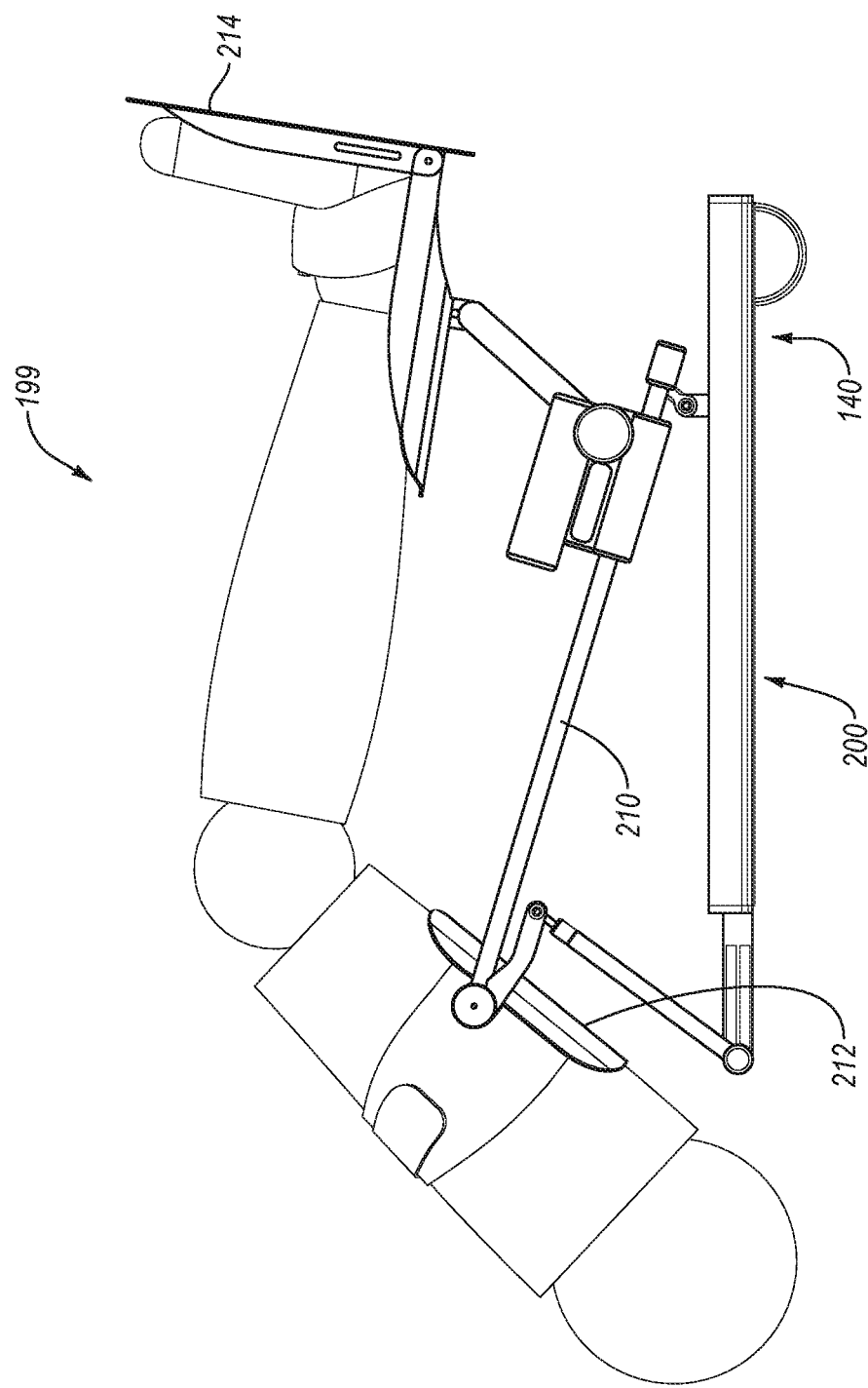

In FIGS. 2-3B, an exemplary embodiment of a continuous passive motion device 199 in accordance with the present invention is shown. The continuous passive motion device 199 includes a base 200, a system of support rods 210, an upper leg support 212 for supporting a patient's upper leg, a lower leg support 214 for supporting a patient's lower leg, and a controller 250. In at least one implementation, the processing unit 140 of FIG. 1 is integrated within the controller 250.

FIG. 2 also depicts an upgraded circuit board 260. In at least one implementation of the present invention, a conventional continuous passive motion device 199 can be upgraded such that it can communicate with a mobile computing device 100. One will understand that a conventional continuous passive motion device 199 may lack the electronic components required to communicate with the mobile computing device 100 (e.g., wireless antennas). Additionally, a conventional continuous passive motion device 199 may lack the software, or even the ability to run the software, necessary to receive commands from a mobile computing device 100.

Accordingly, in at least one implementation of the present invention, a novel upgraded circuit board 260 is provided that can be attached to a conventional continuous passive motion device 199. Specifically, the updated circuit board 260 may replace a circuit board in the conventional continuous passive motion device 199, may replace a circuit board within a controller 250, or it may otherwise attach to the conventional continuous passive motion device 199. One will understand that in order to interface with the variety of different conventional continuous passive motion devices 199 available, in at least one implementation, a unique upgraded circuit boards 260 may be required for each type of conventional continuous passive motion device 199. As such, at least one novel feature of the present invention is the method of replacing a circuit board within a conventional continuous passive motion device 199 with an upgraded circuit board 260 that provides the various functionalities disclosed herein. In contrast, in at least one implementation, a universal upgraded circuit board 260 can be provided that will interface with a wide variety of different continuous passive motion devices 199. In particular, the universal upgraded circuit boards may comprise firmware that is configured to automatically adapt to various particular models.

Accordingly, in various implementations, the continuous passive motion device 199 can be utilized to control and assist a patient in bending a joint to various angles. In particular, the continuous passive motion device 199 can be used to bend a joint to a predetermined angle, hold the angle for a predetermined period of time, and then relax the angle. One will understand that while the continuous passive motion device 199 depicted in this application is knee-specific, in at least one implementation, continuous passive motion devices can be created for different joints within the body.

Figure 4:
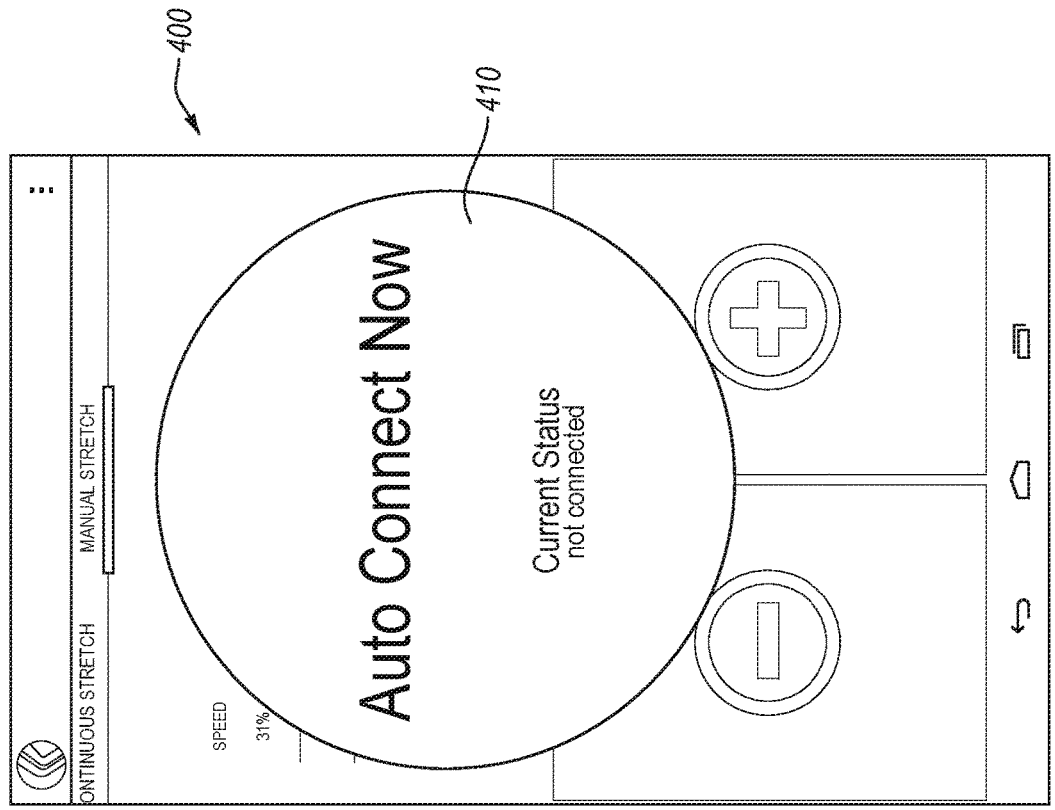
FIG. 4 depicts an implementations of a user interface in accordance with the present invention.

While conventional continuous passive motion devices have been known in the art, systems for controlling the continuous passive motion device in an efficient manner while at the same time tracking patient usage of the continuous passive motion device are not available. As such, FIG. 4 depicts an implementation of the user interface for a mobile computing device 100 in accordance with implementations of the present invention. In particular, the user interface 400 of FIG. 4 comprises a connection interface. The connection interface 400 can provide a user with various configurations and commands for connecting the mobile computing device 100 to a continuous passive motion device 199.

As depicted, the connection user interface 400 comprises an auto connect element 410. The auto connect element 410 can be automatically displayed each time the connection user interface 400 is opened. The auto connect element 410 can indicate to a user that the mobile computing device 100 is automatically scanning for the presence of a continuous passive motion device 199. For example, the auto connect element 410 may comprise a Bluetooth connection indicator that indicates whether the mobile computing device 100 has detected a Bluetooth signal from a continuous passive motion device 199 of interest.

The auto connect element 410 can indicate that multiple continuous passive motion devices 199 are detected. In at least one implementation, however, the mobile computing device 100 is configured to only connect to specific continuous passive motion devices 199. For instance, when initially connecting to a continuous passive motion device 199, the mobile computing device 100 may require a pairing operation and/or a passcode. As such, when detecting multiple continuous passive motion devices 199, the mobile computing device 100 may only connect to the continuous passive motion device 199 that it has previously paired with or received a password for. Additionally, in at least one implementation, the mobile computing device 100 can simultaneously connect to multiple continuous passive motion devices 199.

Figure 5:
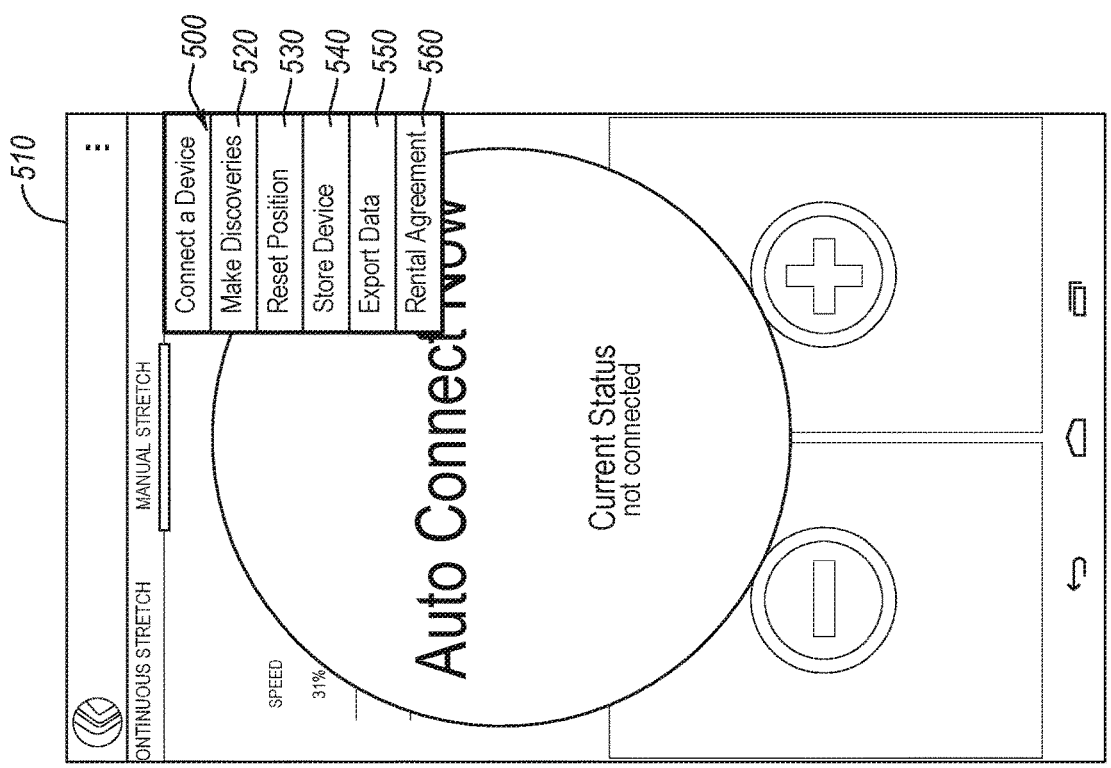
FIG. 5 depicts an implementations of another user interface in accordance with the present invention.

FIG. 5 depicts an implementation of the user interface comprising a menu 500. The menu 500 comprises options for connecting a device 510, making the mobile computing device discoverable 520, resetting the position of the continuous passive motion device 530, positioning the continuous passive motion device for storage 540, exporting data 550, and displaying a rental agreement 560. Additional implementations may comprise fewer or additional menu options beyond those mentioned. Additionally, the previously mentioned menu options may be otherwise combined or accessed through various menu and submenu interfaces.

Figure 6:
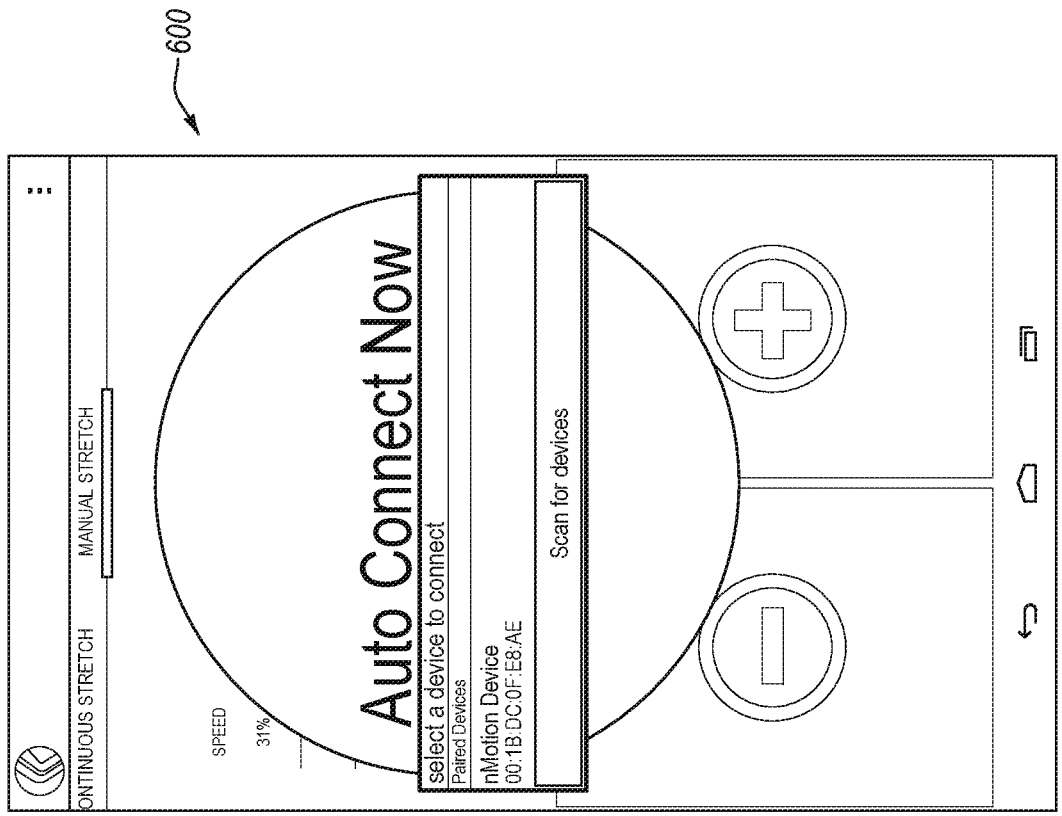
FIG. 6 depicts an implementations of another user interface in accordance with the present invention.

Upon selecting the connect a device menu option 500, the user interface of FIG. 6 can be displayed. FIG. 6 depicts a device connection user interface 600. In particular, the device connection user interface 600 comprises a listing of continuous passive motion devices 199 that are detectable by the mobile computing device 100. The continuous passive motion devices 199 may be detectable through a Wi-Fi network, a Bluetooth connection, a USB connection, some other wireless connection, or any other communication medium capable of transmitting data between the mobile computing device 100 and the continuous passive motion device 199.

Within the device connection user interface 600, a user can select one or more devices to communicate with through the mobile computing device 100. In at least one implementation, upon selecting a particular continuous passive motion device 199 a user must enter a passcode in order to complete the connection. Additionally, in at least one implementation, a user must first activate a connection setting on the continuous passive motion device 199 before the continuous passive motion device 199 is discoverable by the mobile computing device 100.

Figure 7:
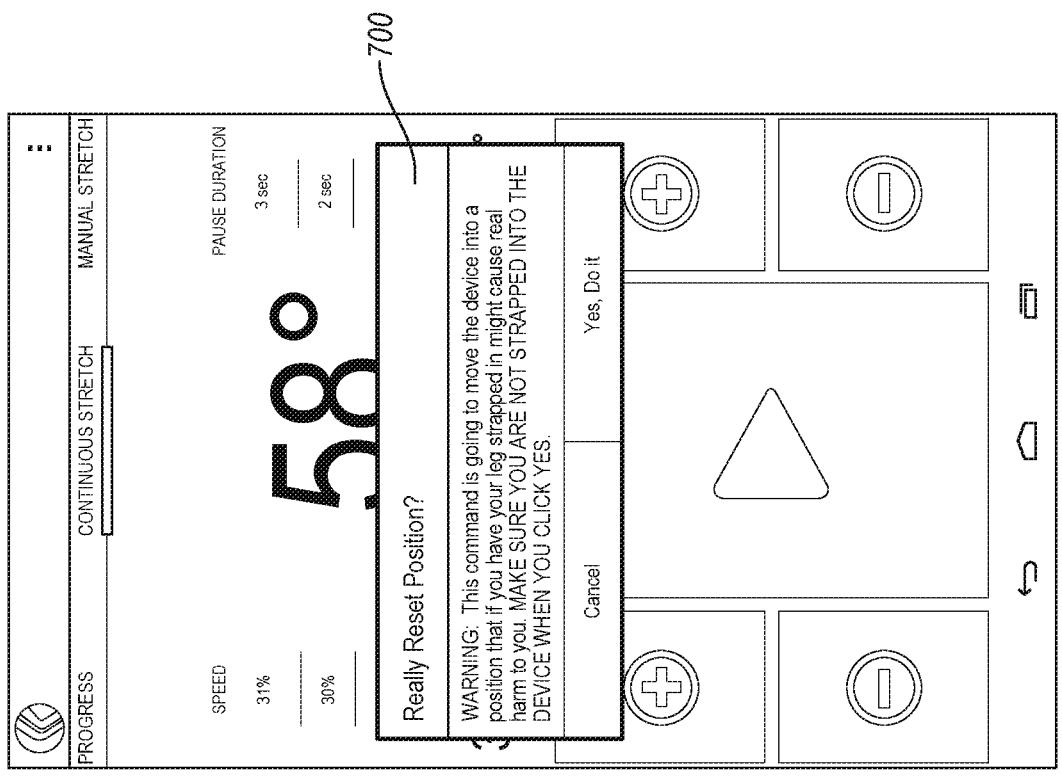
FIG. 7 depicts an implementations of another user interface in accordance with the present invention.

Returning to the menu options of FIG. 5, upon selecting the reset position menu option 530 a user may be displayed the user interface of FIG. 7. FIG. 7 comprises a warning prompt 700 that indicates to a user that he or she is about to initiate a potentially harmful set of motions by the continuous passive motion device 199. Specifically, a reset position may comprise a position of the continuous passive motion device 199 that is convenient for attaching the continuous passive motion device 199 a patient's limb. For example, in at least one implementation, the reset position may comprise positioning the continuous passive motion device 199 into a 90° angle. This may be useful, for example, for a patient whose knee was braced at a 90° angle following surgery. As such, the patient could easily position his or her knee within the continuous passive motion device 199 while the continuous passive motion device 199 is in the reset position.

In at least one implementation, the reset position can be adjusted on a patient-by-patient basis and an orthopedic-structure-by-orthopedic-structure basis. For example, a first patient may require a reset position of 110° while a second patient requires a recent position of 45°. As such, the patient and/or a medical care provider can set a reset position for a particular continuous passive motion device 199.

Returning to FIG. 7, when the reset position option 530 is selected, the mobile computing device 100 can display a warning 700 that the continuous passive motion device 199 will be positioned to a reset position. The warning 700 may provide an indication that it may be harmful for a patient to have a limb with a continuous passive motion device 199 while the continuous passive motion device 199 is being adjusted to the reset position. For example, the continuous passive motion device 199 may reposition itself at a speed or an angle that could be harmful to the patient.

Figure 8:
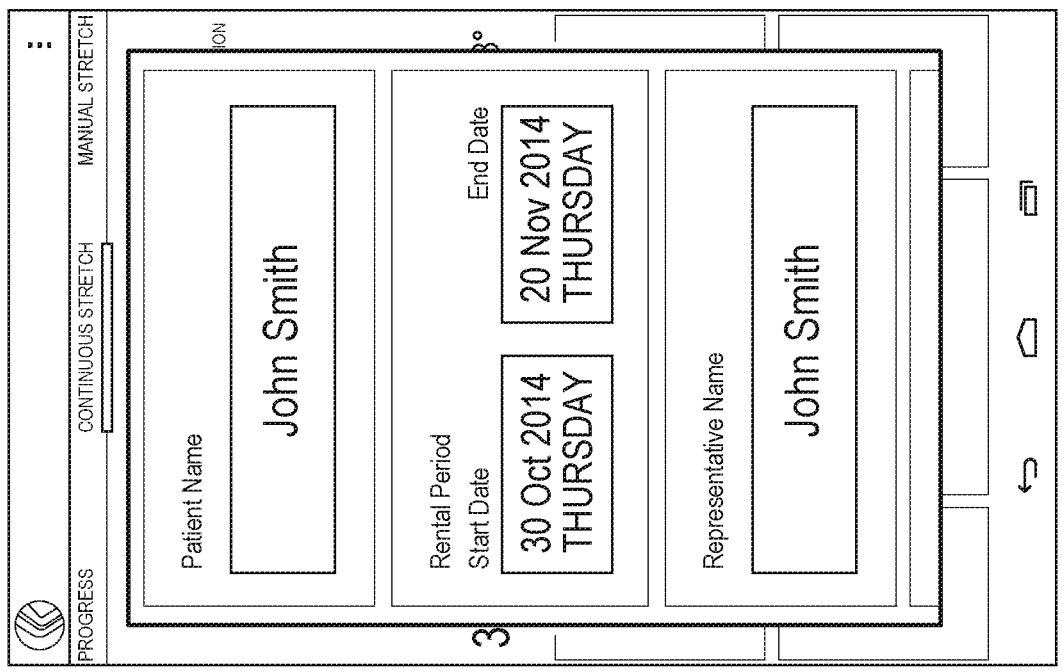
FIG. 8 depicts an implementations of another user interface in accordance with the present invention.

Returning again to FIG. 5, upon selecting the rental agreement option 560, the user interfaces of FIG. 8 may be displayed to a user on the mobile computing device 100. FIG. 8 depicts information boxes containing information about the patient, information about the rental, and information about a rental representative. In at least one implementation, the continuous passive motion devices 199 and mobile computing devices 100 can be rented out to patients for at-home physical therapy use. Medical device rental companies rent many of these devices for specific periods of time. Accordingly, a rental company representative may come to a patient's home to demonstrate use of the device and leave the device with the patient under a rental agreement.

The user interface of FIG. 8 provides a patient with the reminder about the rental and a reminder about the representatives contact information. For example, in at least one implementation, selecting the representative's name within the interface of FIG. 8 can automatically contact the representative, provide contact information for the representative, or open an email prompt for contacting the representative. Additionally, in at least one implementation, a user can be notified by the mobile computing device 100 once the rental period expires. The notification may comprise information on how to return the device and who to contact if the patient has any questions.

Additional features available within the menu 500 of FIG. 5 may include an option for positioning the device in a storage position and an option for exporting data from the mobile computing device 100. Positioning the device within a storage position can include sending a command to the continuous passive motion device 100 to position itself at an angle that is either highly compact or most convenient for storage. For example, the continuous passive motion device 199 of FIG. 1 may be most convenient to store when it is positioned with a 90° angle. In contrast, at least one implementation the continuous passive motion device 199 may be easiest to store when it is positioned at a 0° angle. Accordingly, various different continuous passive motion devices 199 can each be associated with a particular storage angle that is most convenient for the particular device.

The export data option 550 can comprise gathering usage data relating to the usage of a particular continuous passive motion device 199, packaging the usage data, and exporting the usage data to an external destination. In at least one implementation, exporting the data causes the mobile computing device 100 to automatically upload various historical usage data to a remote server. Additionally, in at least one of implementation, exporting the usage data causes the mobile computing device 100 to export the data within a common file format, such as a comma separated value format. Further, in at least one implementation, usage data from multiple different patients can be contained within a single mobile computing device 100. In at least one implementation, exporting the data causes an option to be displayed on a mobile computing device asking a user to indicate which patient's data should be exported. In contrast, in at least one implementation, all patients' data is exported in separate files or in identifiable portions of a single file.

Figure 9:
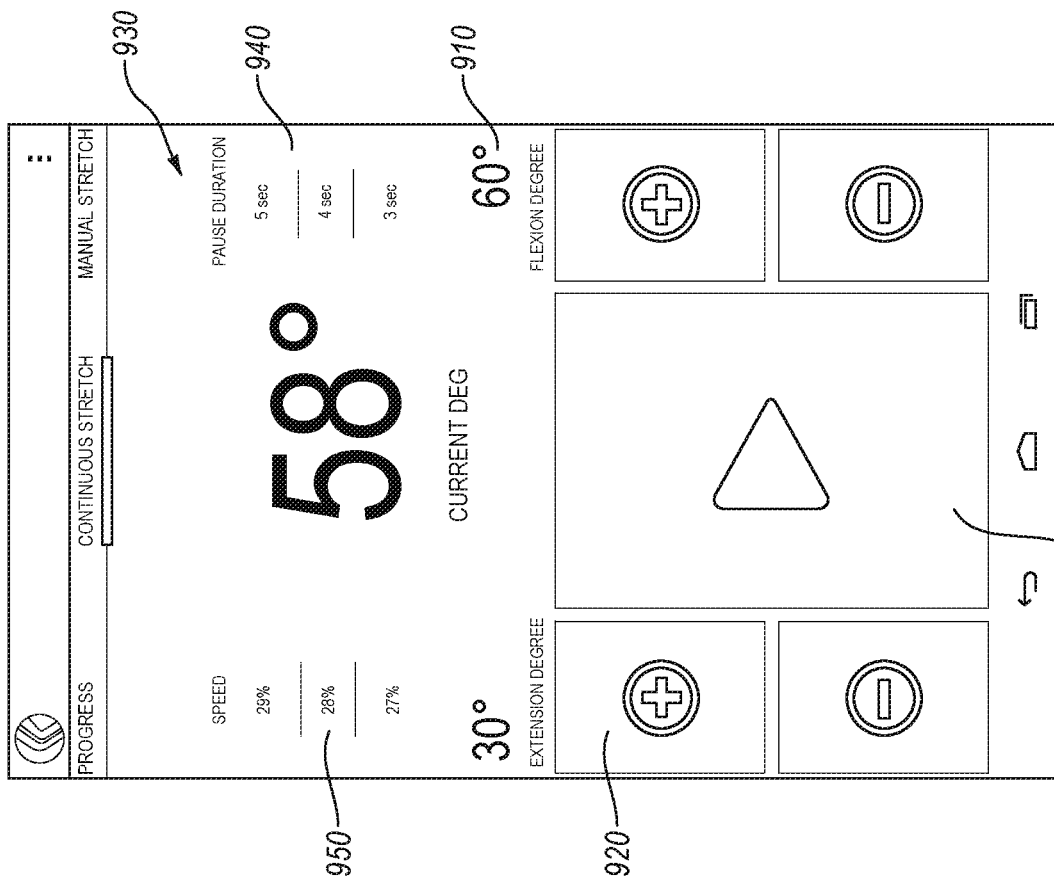
FIG. 9 depicts an implementations of another user interface in accordance with the present invention.

FIG. 9 depicts an implementation of the user interface for controlling a continuous passive motion device 199. In particular, FIG. 9 depicts an activation button 900, a flexion control portion 910, and an extension control portion 920. Additionally the user interface of FIG. 9 depicts a current status information portion 930 that depicts information about the current state of the continuous passive motion device 199.

In at least one implementation, both the extension control portion 920 and the flexion control portion 910 provide a user with the ability to adjust the various degrees to which the continuous passive motion device 199 operates. For example, the extension portion 920 depicts a requested angle of 30°, while the flexion control portion 910 depicts a requested flexion angle of 60°. Both of the respective control sections 920, 910 comprise plus and minus buttons to increase or decrease each respective angle goal. In alternate implementations, however, additional or different means of adjusting an angle can be provided.

In addition to providing control over the flexion and extension angles, the user interface can also comprise a speed control portion 950 and a pause duration control portion 940. The speed control portion 950 can provide controls for a user to dictate the speed at which the continuous passive motion device 199 moves from a first position to a second position. The pause duration portion 940 can provide a user with the ability to dictate the amount of time that the continuous passive motion device 199 pauses once it has reached a final angle. For example, once a continuous passive motion device 199 has reached a 60° flexion angle, the continuous passive motion device 199 may pause at that position for four seconds before progressing to a 30° extension angle.

In at least one implementation, a user can adjust one or more attributes relating to the movements of the continuous passive motion device 199 and have them implemented in real time. For example, an initial extension angle of 45° may be set within the mobile computing device 100. As the continuous passive motion device 199 moves to the 45° angle, a user may decrease the extension angle to 30°. In at least one implementation, the continuous passive motion device 199 can seamlessly transition to the 30° angle without interruption.

To avoid receiving accidental input from a user, safety features may be implemented within the mobile computing device 100. For example, the mobile computing device may only accept input when a single point of contact is detected. This may prevent accidental input when a user accidentally places an entire hand on the input of the mobile device. As an additional safety feature, in at least one implementation, a user can select the activate button 900 at any time to stop or start the movement of the continuous passive motion device 199. Additional safety features such as speed limitations, angle limitations, and force limitations can also be built into both the mobile computing device 100 and the continuous passive motion device 199.

Figure 10:
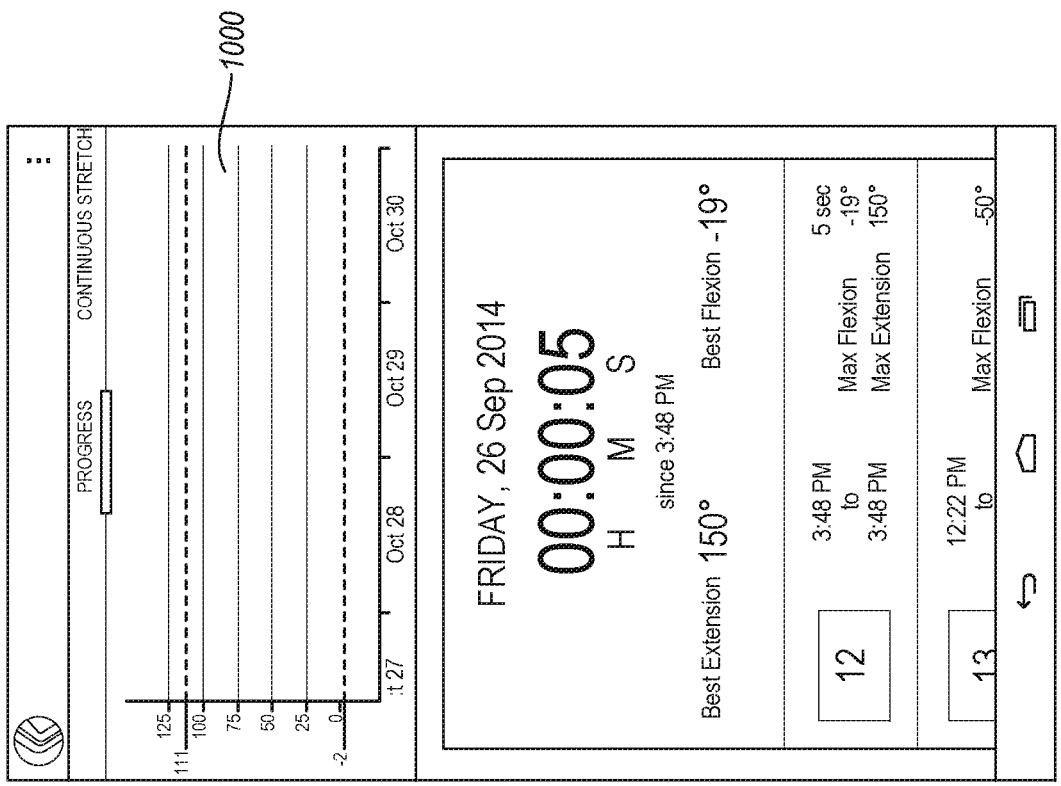
FIG. 10 depicts an implementations of another user interface in accordance with the present invention.

FIG. 10 depicts implementation of a usage data interface 1000. In particular, the usage data interface 1000 comprises historical usage data for a continuous passive motion device 199. The historical usage data can comprise information specifying the periods of time and durations of time that the continuous passive motion device was used, the best extension angle and best flexion angles that were achieved for each period of time, the best extension angles and the best flexion angles that were achieved over the tracked usage of the device, and other similar usage information. Additionally, in at least one implementation, the usage information can be displayed in a graph form. A graph form may be beneficial both to a patient and to a healthcare provider in visually depicting patient improvement throughout the use of the continuous passive motion device 199.

Accordingly, FIGS. 1-10 and the corresponding text illustrate or otherwise describe one or more methods, systems, and/or instructions stored on a storage medium for communicating with a continuous passive motion device using a mobile computing device. One will appreciate that implementations of the present invention can also be described in terms of methods comprising one or more acts for accomplishing a particular result. For example, FIGS. 11 and 12, and the corresponding text, illustrate flowcharts of a sequence of acts in a method for retrofitting a continuous passive motion device and gathering information relating to the use of a continuous passive motion device. The acts of FIGS. 11 and 12 are described below with reference to the components and modules illustrated in FIGS. 1-10.

Figure 11:
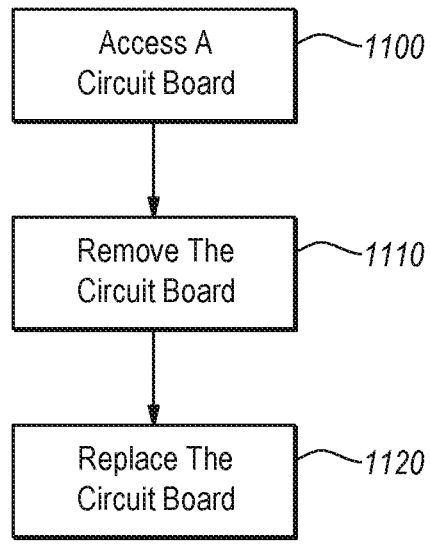
FIG. 11 is a flowchart of an exemplary method implemented by one or more embodiments of the invention.
Figure 12:
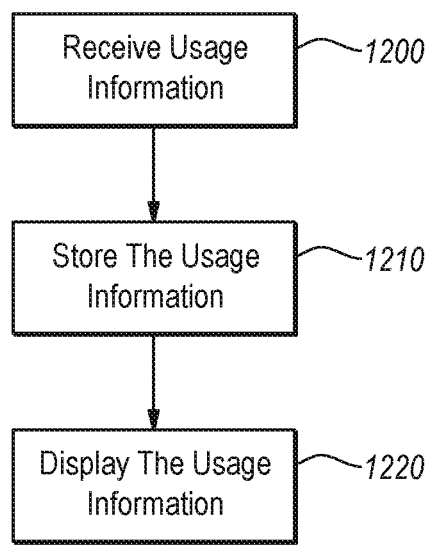
FIG. 12 is a flowchart of another exemplary method implemented by one or more embodiments of the invention.
Figure 13:
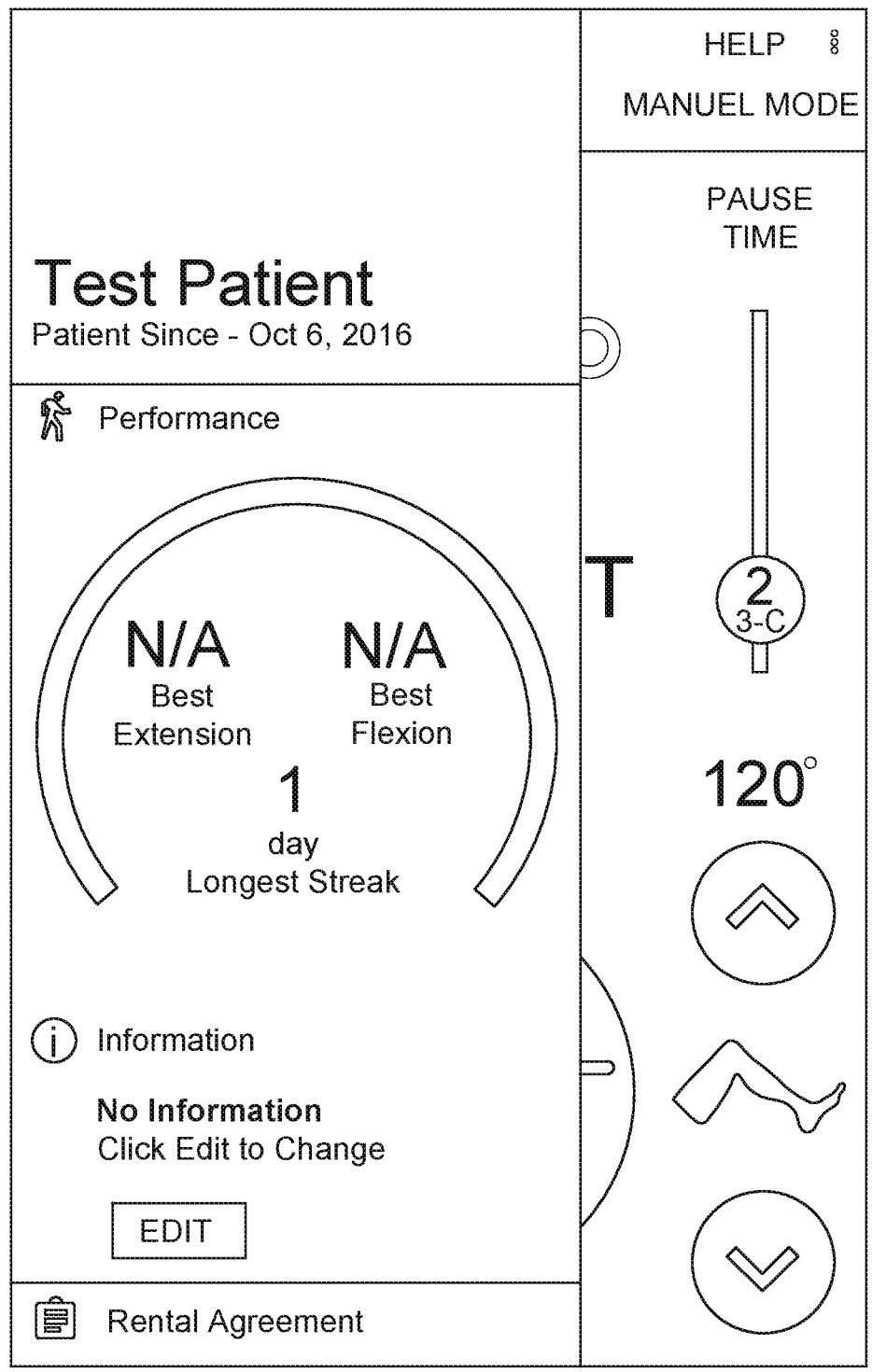
FIGS. 13-18 depict various user interfaces for interacting with a retrofitted continuous passive motion device.
Figure 14:
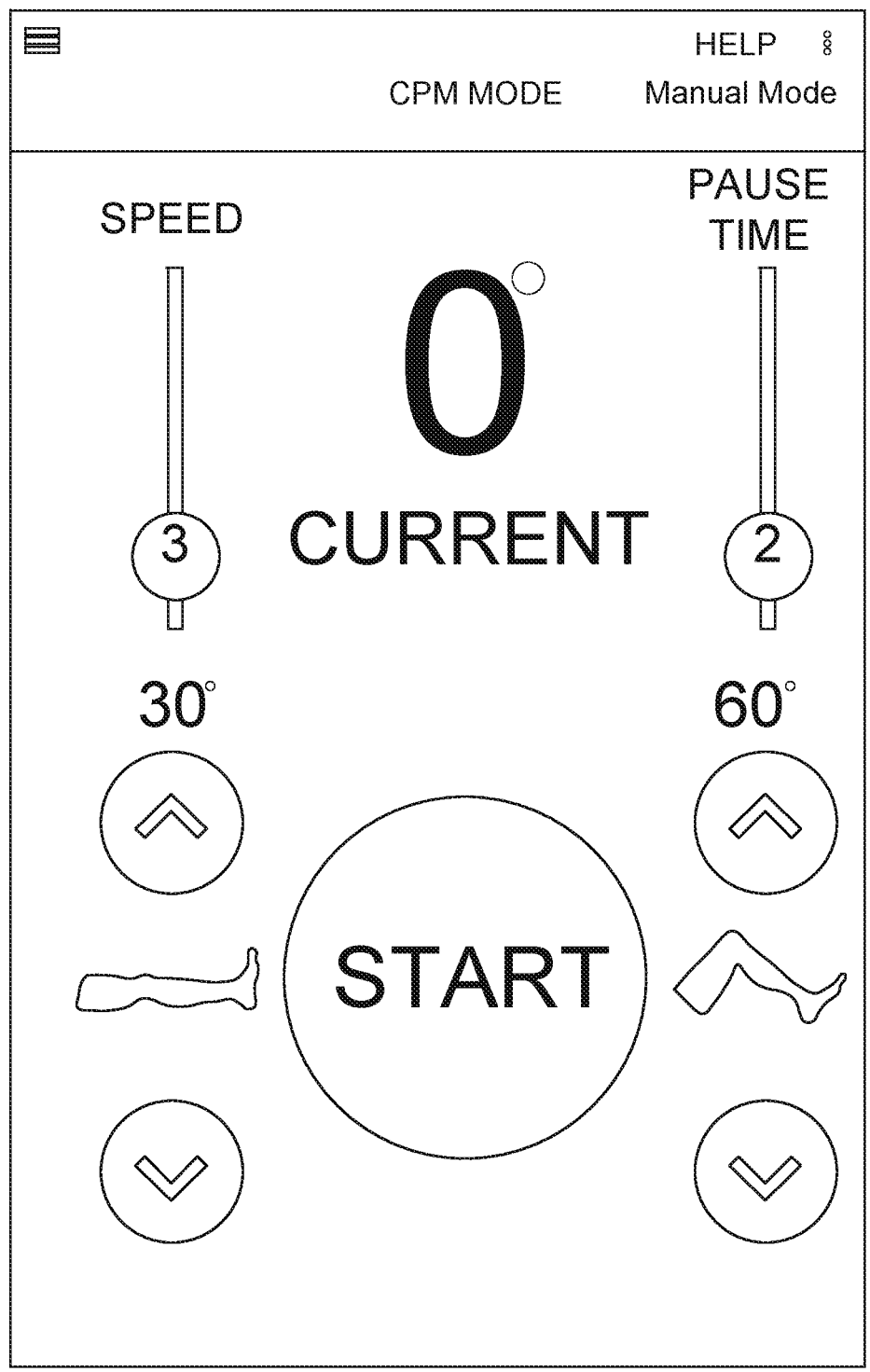
Figure 15:
Figure 16:
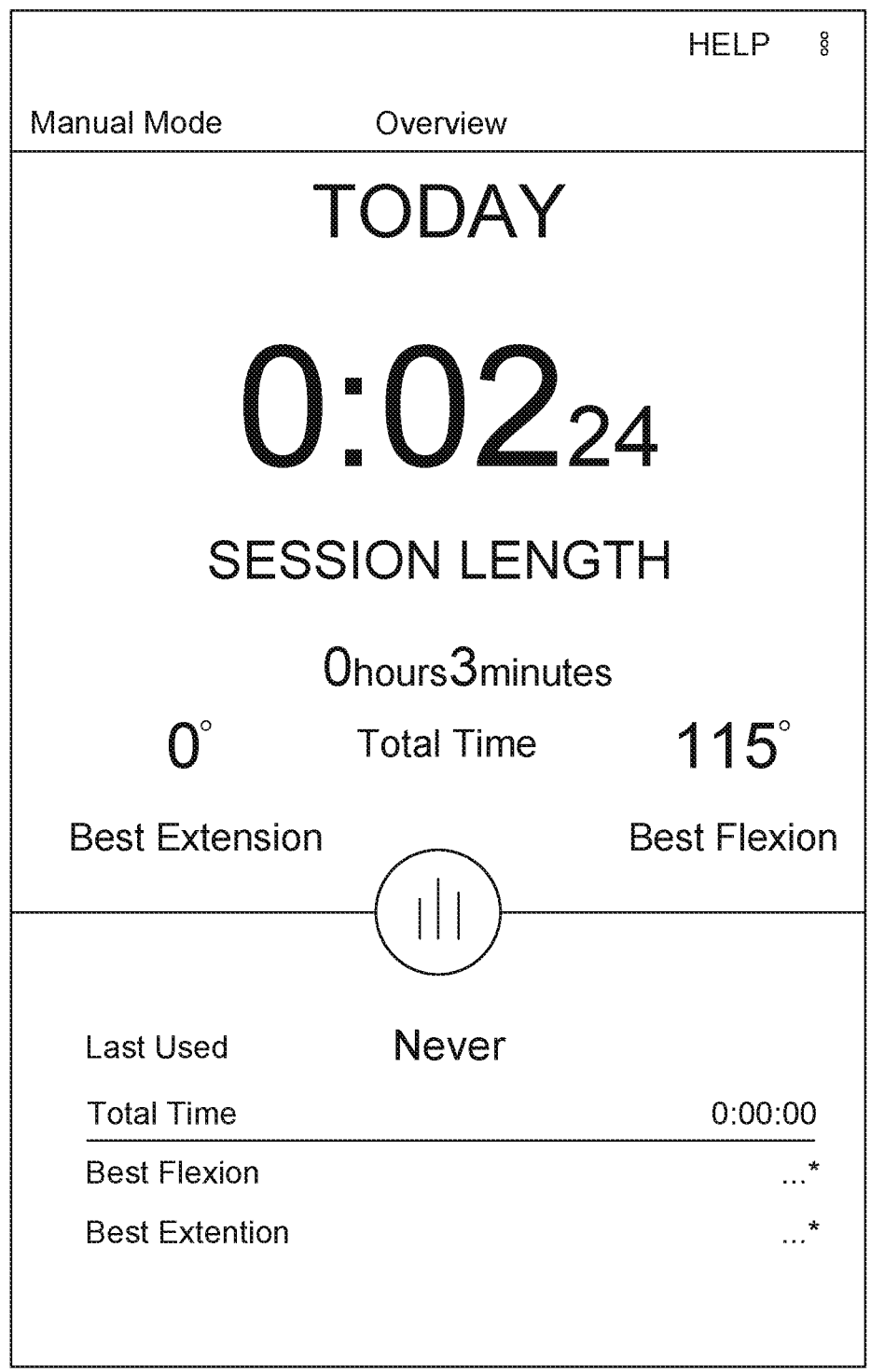
Figure 17:
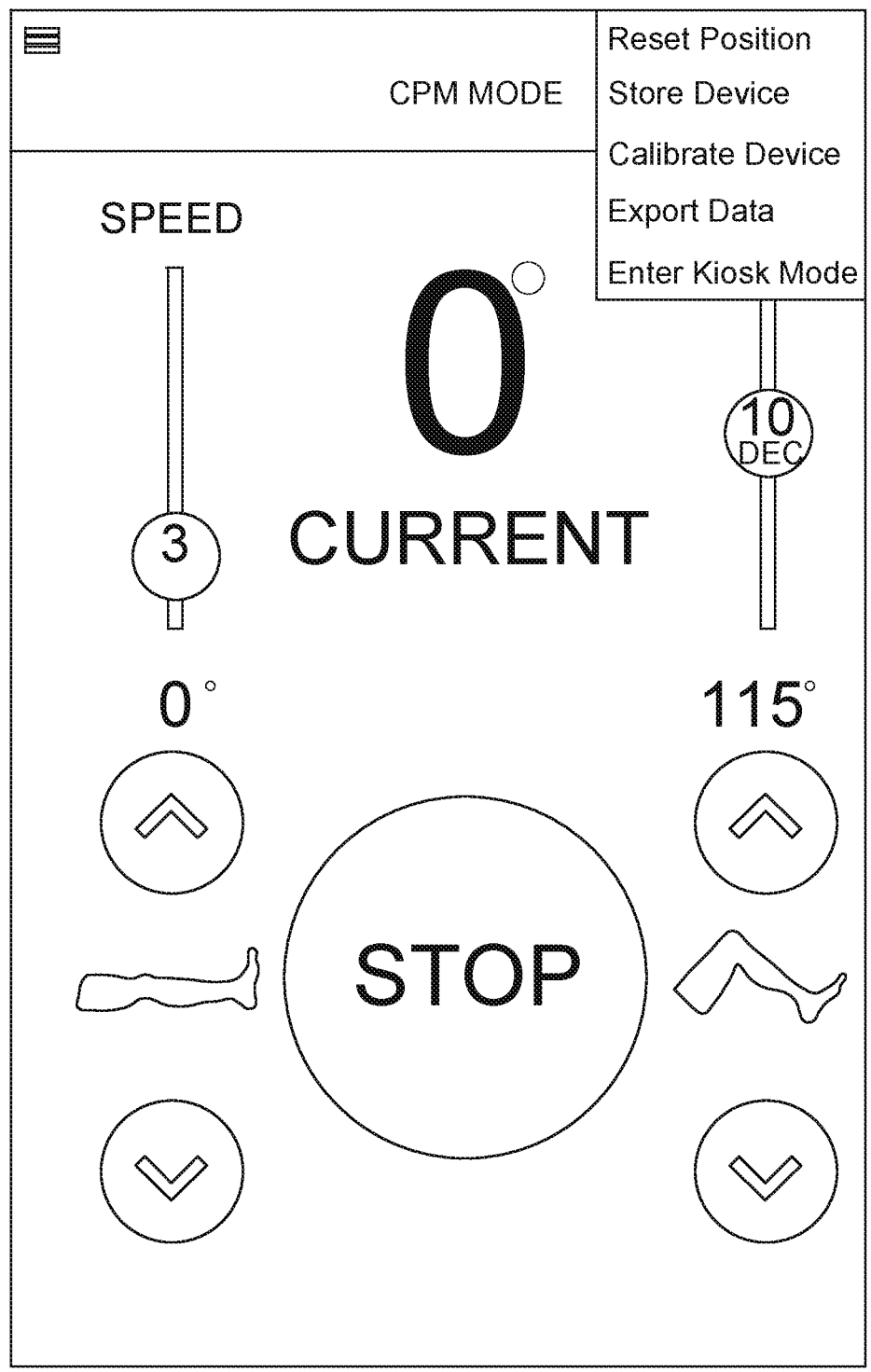
Figure 18:
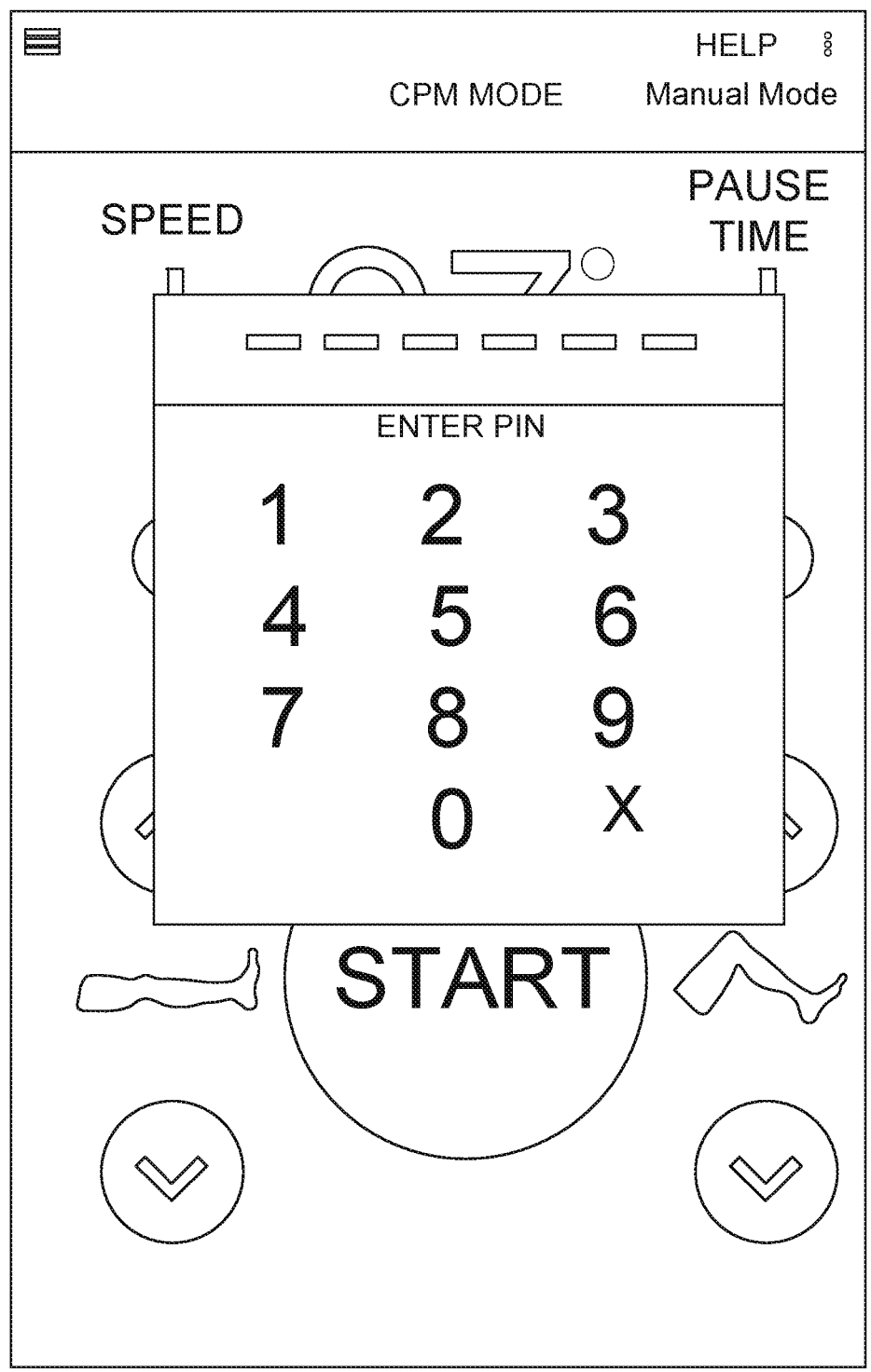

For example, FIG. 11 illustrates that a flow chart for an implementation of a method for retrofitting a continuous passive motion device can comprise an act 1100 of accessing a circuit board. Act 1100 can comprise accessing a control circuit board within the continuous passive motion device. The control circuit board can control the movements of one or more motors within the continuous passive motion device. For example, FIG. 2 depicts both a remote 250 and a processing unit 140. In at least one implementation, an individual can remove a control circuit board from either the remote 250 or the processing unit 140. Additionally, in at least one implementation, removing the control circuit board comprises removing an individual circuit board, while in an alternate implementation removing the control circuit board comprises removing an entire component (e.g., remote 250) that contains the control circuit board.

Additionally, FIG. 11 shows that the method can include an act 1110 of removing the circuit board. Act 1110 can comprise removing the control circuit board from the continuous passive motion device. For example, a user can remove the processing unit 140 and/or the remote control 250 from the continuous passive motion device 199 of FIG. 2.

Further, FIG. 11 shows that the method can include an act 1120 of replacing the circuit board. Act 1120 can comprise replacing the removed control circuit board with an upgrade circuit board. The upgrade circuit board can comprise a circuit board processing unit that is configured to communicate usage information from the continuous passive motion device to an external general purpose-computing device. For example, a circuit board in the processing unit 140 and/or the remote 250 of FIG. 2 can be replaced with the upgraded circuit board 260. Once the conventional continuous passive motion device has been upgraded, the continuous passive motion device may be able to communicate with the mobile computing device 100 through the upgraded circuit board 260.

In an additional implementation, FIG. 12 shows that a method for gathering information relating to the use of a continuous passive motion device can include an act 1200 of receiving usage information. Act 1200 can comprise receiving usage information from a continuous passive motion device processing unit. The usage information can comprise at least one duration of time that the continuous passive motion device was used. For example, the continuous passive motion device 199 of FIG. 1 can communicate usage information to the mobile computing device 100 through a network 110. In at least one implementation, the usage information can comprise information about when the continuous passive motion device was used as depicted in FIG. 10.

Additionally, FIG. 12 shows that the method can include an act 1210 of storing the usage information. Act 1210 can comprise storing the usage information such that the usage information is available within a historical dataset. For example, the stored usage information can be stored within a historical dataset as depicted in FIG. 10, where multiple sessions of use are stored.

Further, FIG. 12 shows that the method can include an act 1220 of displaying the usage information 1220. Act 1220 can comprise displaying at least a portion of the usage information from the historical dataset on a graphical user interface. For example, FIG. 10 displays a graph of the flexion and extension angles achieved over the use of the continuous passive motion device.

Additionally, FIGS. 13-18 shows various implementations of user interfaces for interacting with and controlling a retrofitted continuous passive motion device. For example, once retrofitted, a continuous passive motion device can be controlled in various aspects through a touch interface as indicated by the user interfaces.

Figure 19:
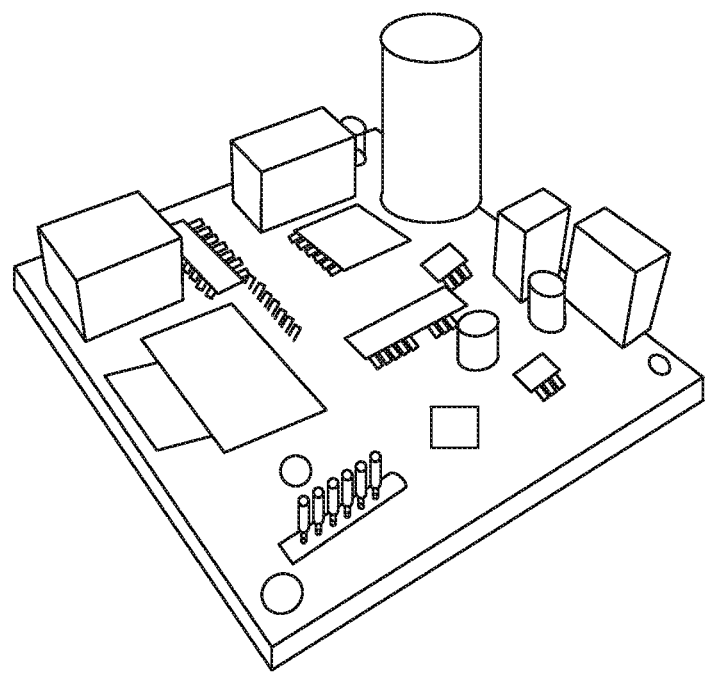
FIG. 19 depicts an implementation of a retrofit circuit board.

FIG. 19 depicts an implementation of a retrofit circuit board in accordance with implementations of the present invention. Specifically, the circuit board can be connected to control circuits within a variety of different continuous passive motion devices. Once connected, the retrofit circuit board can provide the retrofitted device with a significant increase in functionality and data tracking, as described above.

Accordingly, various implementations of the present invention provide significant and novel benefits in both controlling a continuous passive motion device and in gathering usage data. In particular, implementations of the present invention include upgrading a conventional continuous passive motion device such that is can also communicate with general-purpose computing devices of the present invention.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

Embodiments of the present invention may comprise or utilize a special-purpose or general-purpose computer system that includes computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("S aaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some embodiments, such as a cloud-computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthopedic stretching device for rehabilitation of joints, the orthopedic stretching device comprising:
  a removable control circuit board including a processor, wherein the removable control circuit board controls the movements of one or more motors for moving portions of the orthopedic stretching device; and
  an upgraded control circuit board including a wireless communication device, a processor, and computer-readable media, wherein the removable control circuit board is replaceable by the upgraded control circuit board to control the movements of one or more motors;
  wherein the computer-readable media includes computer-executable instructions that, when executed by the processor of the upgraded control circuit board, cause the orthopedic stretching device to communicate with a mobile general purpose computing device via the wireless communication device;
  and wherein the communication with the mobile general purpose computing device includes usage information comprising at least one duration of time that the orthopedic stretching device was operated.

* * * * *